(12) United States Patent
Wang et al.

(10) Patent No.: US 8,565,859 B2
(45) Date of Patent: Oct. 22, 2013

(54) METHOD AND SYSTEM FOR IMAGE BASED DEVICE TRACKING FOR CO-REGISTRATION OF ANGIOGRAPHY AND INTRAVASCULAR ULTRASOUND IMAGES

(75) Inventors: Peng Wang, Princeton, NJ (US); Simone Prummer, Neunkirchen am Brand (DE); Terrence Chen, Princeton, NJ (US); Dorin Comaniciu, Princeton Junction, NJ (US); Olivier Ecabert, Pretzfeld (DE); Martin Ostermeier, Buckenhof (DE)

(73) Assignee: Siemens Aktiengesellschaft, Munich (DE)

( * ) Notice: Subject to any disclaimer, the term of this patent is extended or adjusted under 35 U.S.C. 154(b) by 54 days.

(21) Appl. No.: 13/171,560

(22) Filed: Jun. 29, 2011

(65) Prior Publication Data

US 2012/0059253 A1 Mar. 8, 2012

Related U.S. Application Data

(60) Provisional application No. 61/359,431, filed on Jun. 29, 2010.

(51) Int. Cl.
*A61B 5/05* (2006.01)
*A61B 8/14* (2006.01)
*G06K 9/00* (2006.01)

(52) U.S. Cl.
USPC ............ 600/427; 600/462; 600/467; 382/128

(58) Field of Classification Search
USPC .......... 600/427, 466, 467, 462; 382/128, 276, 382/294, 291, 286
See application file for complete search history.

(56) References Cited

U.S. PATENT DOCUMENTS

| | | |
|---|---|---|
| 2005/0196028 A1 | 9/2005 | Kleen et al. |
| 2006/0241465 A1* | 10/2006 | Huennekens et al. ........ 600/458 |
| 2007/0043292 A1 | 2/2007 | Camus et al. |
| 2008/0051660 A1 | 2/2008 | Kakadaris et al. |
| 2008/0177183 A1 | 7/2008 | Courtney et al. |

OTHER PUBLICATIONS

Wang et al., "Robust Guidewire Tracking in Fluoroscopy", IEEE, 2009, pp. 691-698.*
Bruining, Nico, et al., "Intravascular Ultrasound Registration/Integration with Coronary Angiography", Cardiology Clinics, vol. 27, Issue 3, pp. 531-540, Aug. 2009.

* cited by examiner

*Primary Examiner* — Long V. Le
*Assistant Examiner* — Katherine Fernandez

(57) ABSTRACT

A method and system for co-registration of angiography data and intra vascular ultrasound (IVUS) data is disclosed. A vessel branch is detected in an angiogram image. A sequence of IVUS images is received from an IVUS transducer while the IVUS transducer is being pulled back through the vessel branch. A fluoroscopic image sequence is received while the IVUS transducer is being pulled back through the vessel branch. The IVUS transducer and a guiding catheter tip are detected in each frame of the fluoroscopic image sequence. The IVUS transducer detected in each frame of the fluoroscopic image sequence is mapped to a respective location in the detected vessel branch of the angiogram image. Each of the IVUS images is registered to a respective location in the detected vessel branch of the angiogram image based on the mapped location of the IVUS transducer detected in a corresponding frame of the fluoroscopic image sequence.

33 Claims, 12 Drawing Sheets

METHOD AND SYSTEM FOR IMAGE BASED DEVICE TRACKING FOR CO-REGISTRATION OF ANGIOGRAPHY AND INTRAVASCULAR ULTRASOUND IMAGES

This application claims the benefit of U.S. Provisional Application No. 61/359,431, filed Jun. 29, 2010, the disclosure of which is herein incorporated by reference.

BACKGROUND OF THE INVENTION

The present invention relates to image based device detection and tracking, and more particularly, image based device detection and tracking for co-registration of angiographic fluoroscopic images and intravascular ultrasound images.

Angiography and Intravascular ultrasound (IVUS) are two widely used modalities to image coronary vessels in coronary interventions. Both modalities have various advantages. X-ray angiography is a modality that is commonly used to guide percutaneous coronary interventions (PCI). IVUS is an imaging technique in which an ultrasound transducer is attached to an end of a guidewire. The guidewire is first guided through a guiding catheter and from there through the vessels of a patient. The ultrasound transducer is used to obtain ultrasound images from within the vessels. IVUS can be used to obtain images in which an entire cross-section of the interior of the vessel can be seen in a single view. IVUS imaging can be used to provide rich information on vessel wall composition and the extent of plaques present at various points within a vessel. Accordingly, IVUS can be used for tissue characterization, analysis of lesion length, quantification of vessel and lumen diameter, and the estimation of stent expansion. However, the lack of vessel orientation information in IVUS images makes it difficult to fully understand the spatial structure of the vessels.

Accordingly, it is desirable to co-register the angiography and IVUS image modalities in order to combine the high spatial resolution from the IVUS data with the hood overview and orientation within the vessels obtained from the angiography.

BRIEF SUMMARY OF THE INVENTION

Embodiments of the present invention provide a method and apparatus for co-registration of angiography and Intravascular Ultrasound (IVUS) data using image based device detection and tracking. According to various embodiments, an interactive vessel segmentation method can be used to specify the coronary branch where an IVUS catheter will be advanced and pulled back. The vessel segmentation provides a vessel branch with orientations. During the pulling-back stage, the IVUS transducer is detected and tracked in a sequence of fluoroscopic images. The distance between the tracked IVUS transducer and the guiding catheter tip is used to register the IVUS transducer to the stationary segmented vessel. By synchronizing the IVUS images with the fluoroscopic images through time stamps, the corresponding position of each IVUS image along the vessel on an angiogram image can be determined.

In one embodiment of the present invention, a vessel branch is detected in an angiogram image. A sequence of IVUS images is received from an IVUS transducer. The IVUS images are acquired while the IVUS transducer is being pulled back through the vessel branch. A fluoroscopic image sequence is received. The fluoroscopic image sequence is also acquired while the IVUS transducer is being pulled back through the vessel branch. The IVUS transducer and a guiding catheter tip are detected in each frame of the fluoroscopic image sequence. The IVUS transducer detected in each frame of the fluoroscopic image sequence is mapped to a respective location in the detected vessel branch of the angiogram image. Each of the IVUS images is registered to a respective location in the detected vessel branch of the angiogram image based on the mapped location of the IVUS transducer detected in a corresponding frame of the fluoroscopic image sequence.

These and other advantages of the invention will be apparent to those of ordinary skill in the art by reference to the following detailed description and the accompanying drawings.

DETAILED DESCRIPTION

Figure 1:
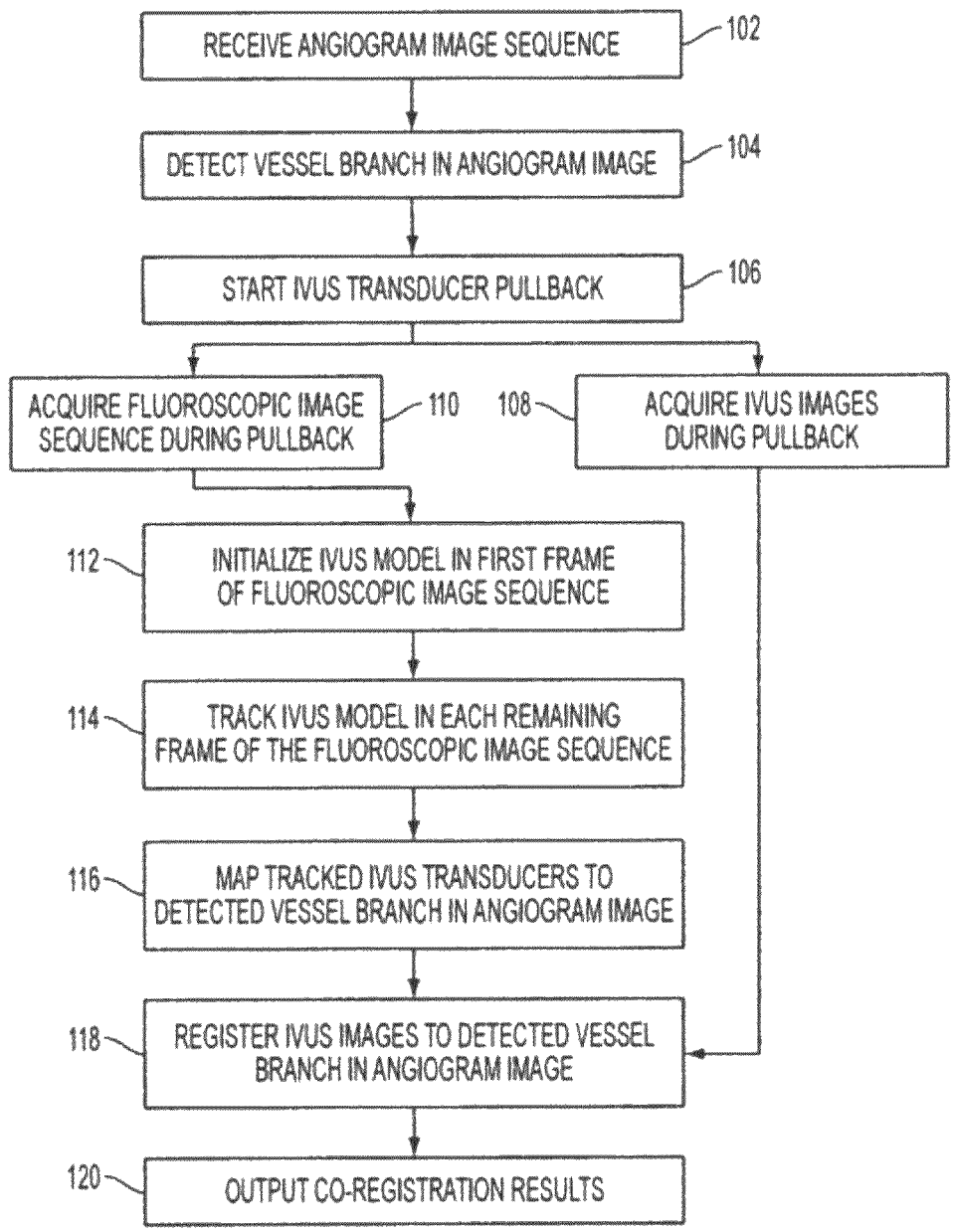
FIG. 1 illustrates a method of co-registering angiography and IVUS images according to an embodiment of the present invention.
Figure 2A:
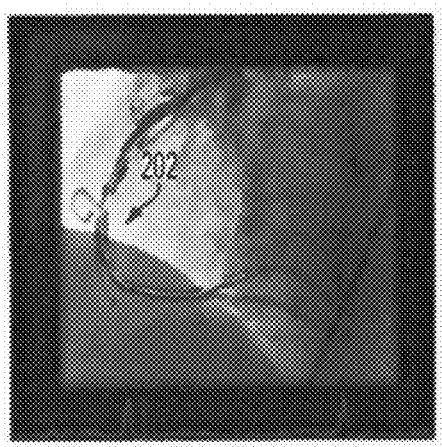
FIG. 2 illustrates exemplary results of various steps of the method of FIG. 1.
Figure 2B:
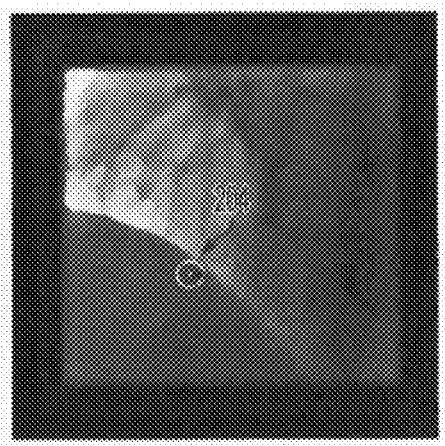
Figure 2C:
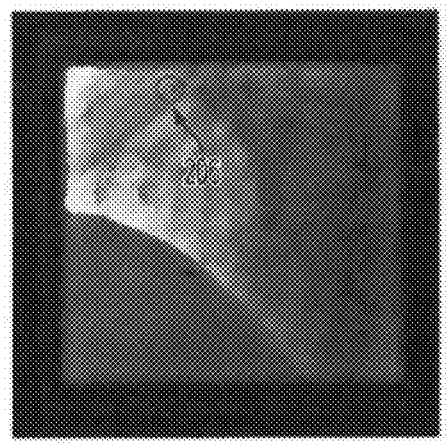
Figure 2D:
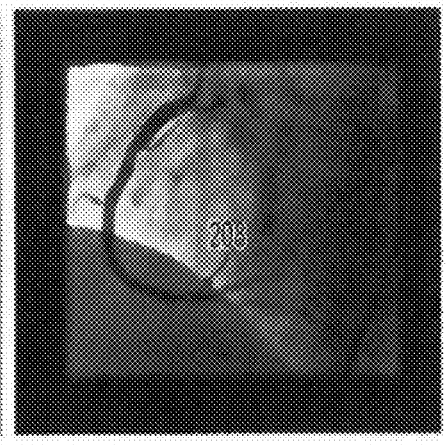

The present invention relates to a method and system for co-registration of angiography and Intravascular Ultrasound (IVUS) images using image based device tracking. Embodiments of the present invention are described herein to give a visual understanding of the co-registration method. A digital image is often composed of digital representations of one or more objects (or shapes). The digital representation of an object is often described herein in terms of identifying and manipulating the object. Such manipulations are virtual manipulations accomplished in the memory or other circuitry/hardware of a computer system. Accordingly, is to be understood that embodiments of the present invention may be performed within a computer system using data stored within the computer system.

Registration of IVUS and angiography images finds the position of each IVUS image plane along a vessel branch during the IVUS pullback. Manuel labeling, which has previously been used to specify the position of IVUS images, can be straightforward and easy to implement. However, manually finding a corresponding landmark between IVUS and angiography data is challenging, as it requires expertise and can be time-consuming. Furthermore, without continuous tracking, previous works typically assume constant IVUS pullback speed to obtain the IVUS imaging plane from linear interpolation. Embodiments of the present invention provide a computational framework for automated image based IVUS tracking in X-ray images to continuously identify the location of the IVUS image plane in order to achieve co-registration of angiography and IVUS images.

Accurate and robust tracking of medical devices in X-ray images is challenging. The devices undergo cardiac motion and breathing motion during interventions. Even with electrocardiogram (ECG) triggering, the breathing motion can still be large. X-ray images, especially fluoroscopic images, usually have a low signal to noise ratio because low doses of radiation are typically preferred in interventional imaging. The appearance of devices can be blurry in X-ray images, and artifacts and cluttered background often exist. Considering all of these factors, conventional tracking methods based on intensity appearance or edge-based energy would encounter difficulties. Embodiments of the present invention provide a framework that utilizes learning based detection and model based probabilistic tracking.

In embodiments of the present invention, learning based detectors that are trained from collected data are used to detect different devices, such as IVUS transducers, guiding catheter body and tips, and the wire that is used to pull the IVUS transducers. The detection results are used as primitive features for subsequent tracking. A probabilistic model based tracking framework can be used to combine detections of different devices in a Bayesian inference framework in order to achieve robust and accurate tracking results. The device tracking results are then used for a geodesic distance based registration during IVUS pullback. Embodiments of the present invention only require minimum user interactions and do not assume a constant IVUS pullback speed.

FIG. 1 illustrates a method of co-registering angiography and IVUS images according to an embodiment of the present invention. The method of FIG. 1 can be divided into two stages: the "angiogram" stage (steps 102 and 104) and the "pullback" stage (steps 106-120). In the angiogram stage, a contrast-enhanced coronary is imaged and a vessel branch where the IVUS imaging will take place is extracted (segmented). In the pullback stage, an IVUS transducer is pulled inside a vessel to obtain a sequence of intravascular images, and fluoroscopic images are acquired to track the movement of the IVUS transducer.

Referring to FIG. 1, at step 102, angiogram image sequence is received. The angiogram images in the sequence are contrast enhanced fluoroscopic images. In particular, a contrast agent is injected into the patient, so vessels appear darker and are clearly visible in the angiogram images. The angiogram image sequence may be received directly from an x-ray imaging device or may be received by loading a previously stored angiogram sequence. A frame of the angiogram image sequence is selected for interactive vessel detection, and at step 104, a vessel branch is detected in the frame of the angiogram image sequence using interactive vessel detection. In particular, an interactive vessel detection method is used to segment a centerline of a vessel branch where the IVUS imaging will be performed, and to extend the centerline toward the guiding catheter. FIG. 2 illustrates exemplary results of various steps of the method of FIG. 1. Image (a) of FIG. 2 shows exemplary results of the interactive vessel detection of step 104 in an angiogram image. As shown in image (a) of FIG. 2, a centerline 202 of a vessel branch is detected in the angiogram image.

Figure 3:
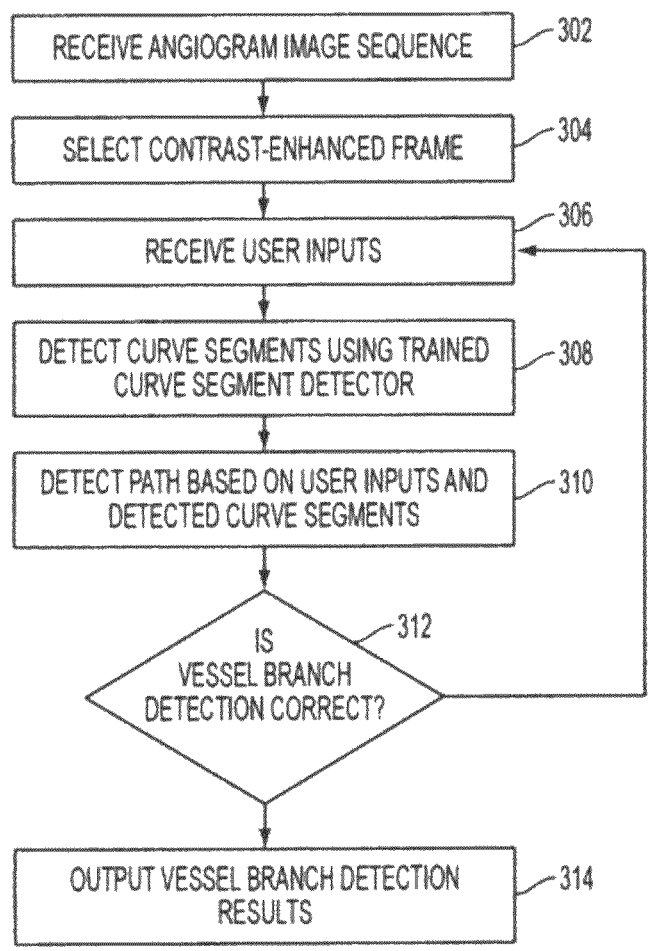
FIG. 3 illustrates a method for interactive vessel detection in the angiogram stage of the method of FIG. 1 according to an embodiment of the present invention.

FIG. 3 illustrates a method for interactive vessel detection in the angiogram stage of the method of FIG. 1 according to an embodiment of the present invention. The method of FIG. 3 provides greater detail for the angiogram stage (steps 102 and 104) of FIG. 1 according to a particular embodiment. Referring to FIG. 3, at step 302, the angiogram image sequence is received. At step 304, a contrast-enhanced frame of the angiogram sequence is selected for vessel segmentation. In an advantageous implementation, a frame at the end-diastole (ED) phase can be selected for vessel segmentation. An electrocardiogram (ECG) signal can be recorded during image acquisition of the angiogram image sequence. The frame at the ED phase can be selected to be synchronized with subsequent fluoroscopic images, which are also acquired at the ED phase through ECG triggering. The frame selection may be performed manually by a clinician. The selected frame should have maximum contrast to better visualize the vessel branch and can be right after the QRS complex to better synchronize with later acquired pulling-back images.

At step 306, user inputs are received to initialize the vessel segmentation. The user inputs can be received via a user input device, such as a mouse. According to a possible implementation, two user inputs can be received specifying a proximal end and a distal end of the vessel branch in which the IVUS imaging will take place. The first user input to identify the proximal end of the vessel is placed at the tip of the guiding catheter into which the IVUS transducer is inserted. The second user input is placed at the distal end of the vessel. Accordingly, the two user inputs should cover the pulling path of the IVUS transducer.

At step 308, curve segments are detected in the angiogram frame using trained curve segment detectors. The interactive detection method combines the user inputs with learning based detections. This method adapts a hierarchical learning based method that is similar to the method presented in U.S. Pat. No. 7,792,342, the disclosure of which is incorporated herein by reference. However, according to an embodiment of the present invention, the detectors used in this method are trained to detect curve segments, not a whole curve. In order to detect the curve segments, a trained piece-wise curve segment detector is first used to detect curves segments, and then a trained pair-wise curve segment detector is used to detect pair-wise connections between the detected curve segments.

The piece-wise curve segment detector detects individual pieces of curves, each a short line segments with a constant length. A curve segment has three parameters $(x,y,\theta)$, where $(x,y)$ is the segment center location and $\theta \in [-90,90]$ is the curve segment orientation. Such a learning based curve segment detector is trained offline using annotated training data. All points on the annotated curves in the training data are considered positive training samples, while negative training samples are randomly obtained from regions other than the annotated curve structures. The piece-wise curve segment detector can be a probabilistic boosting tree (PBT) classifier trained using Haar features. In order to detect segments of different orientations, the angiogram frame is rotated at discrete angles to search the rotation angles of curve segments. The piece-wise curve segment detector determines a probability score for each detected curve segment.

Since the piece-wise curve segment detector typically produces many false alarms, the pair-wise curve segment detector is used to prune false detections. In the pair-wise segment detection, every pair of two detected curve segments are classified to determine a probability that the pair belong to a curve, based on image intensity and geometric features. Such geometric features can include the center distance between the curve segments and the angle difference between the orientations of the curve segments. The piece-wise curve segment detector can also be trained using a PBT classifier based on annotated training data.

At step 310, the centerline of the vessel branch is detected based on the user inputs and the detected curve segments. In particular, an optimum path is detected between the source and destination points specified by the first and second user inputs, respectively, based on the detected curve segments. The path cost is defined based on the pair-wise detection scores along a path, i.e., $\Sigma_{i,j \in L} \log(p_{i,j})$, where $p_{i,j}$ is the probabilistic output from the pair-wise curve segment detector on the i-th and j-th curve segments. To detect a path between two user inputs, each user input creates a new curve segment whose position is defined by the user input and whose orientation is interpolated from neighboring detected curves segments using an extension field. According to an advantageous implementation, the minimization of the path cost can be performed by solving a graph based shortest path problem, in which the geometric constraints are incorporated into the graph based optimization in order to smooth detection results. It is also possible that other techniques, such as Dynamic Programming can be used to minimize the path cost.

Figure 4:
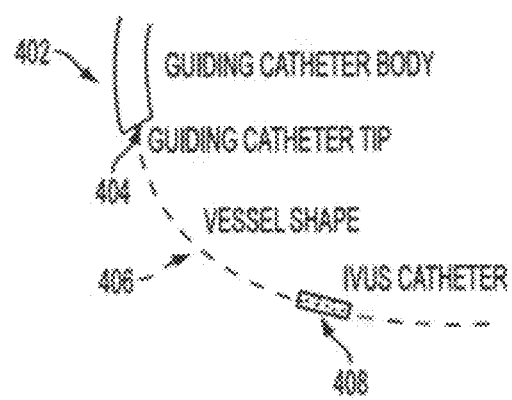
FIG. 4 illustrates exemplary interactive vessel detection results.

At step 312, an indication can be received from a user indicating whether the detection result is satisfactory. If the vessel detection is not satisfactory, the method can return to step 306, where additional user inputs are provided to further constrain the interactive detection method and obtain refined detection results. The user interaction can be repeated until a satisfactory detect result is obtained. If the vessel detection is satisfactory, the method proceeds to step 314 and outputs the detection results. The results can be output by displaying the vessel detection results, for example on a display device of a computer system, or by storing the vessel detection results on a memory or storage of the computer system. According to an embodiment of the present invention, the output vessel detection results can be returned to an angiography and IVUS co-registration algorithm, such as the method of FIG. 1. FIG. 4 illustrates exemplary interactive vessel detection results. As shown in FIG. 4, images 400 and 410 are contrasted enhanced angiogram images and vessel centerlines 402 and 412 are detected in images 400 and 410, respectively.

Returning the FIG. 1, at step 106, pullback of the IVUS transducer is started and the "pullback" stage (steps 106-120) of the method is initiated. In particular, the IVUS transducer has been advanced to the distal end of a target vessel branch, and during pullback, the IVUS transducer is pulled back toward the proximal end by retracting the guidewire back through the guiding catheter. The pullback of the IVUS transducer can be performed manually or by a machine, such as a motor. The IVUS pullback may be performed with or without a constant pullback speed, as embodiments of the present invention do not assume a constant IVUS pullback speed. During the pullback of the IVUS transducer, both IVUS images (step 108) and fluoroscopic images (step 110) are acquired. In the pullback stage, the IVUS transducer and guiding catheter tip are detected and tracked in the fluoroscopic images and mapped back to the detected vessel branch, and the IVUS images are registered to the segmented vessel branch using time synchronization between the fluoroscopic images and the IVUS images. According to an advantageous implementation, steps 108-114 can be performed in real time while the image IVUS transducer is being pulled back, but the present invention is not limited thereto.

At step 108, IVUS images are acquired during the pullback of the IVUS transducer. In particular, IVUS images are continuously acquired by the IVUS transducer as the IVUS transducer is being pulled back through the vessel branch, resulting in a sequence of IVUS images. The IVUS images are ultrasound images taken by the IVUS transducer from within the vessels. Each IVUS image is associated with a timestamp that indicates the respective acquisition time for the image.

At step 110, a fluoroscopic image sequence is acquired during the pullback of the IVUS transducer. The fluoroscopic image sequence is acquired using an X-ray device to continuously obtain x-ray (fluoroscopic) images of the vessel region while the IVUS transducer is being pulled back. Each fluoroscopic image (frame) of the fluoroscopic image sequence is associated with a timestamp that indicates the respective acquisition time for that fluoroscopic image. The fluoroscopic images (step 110) and the IVUS images (step 108) are obtained simultaneously while the IVUS transducer is being pulled back. According to an advantageous implementation, acquisition of the fluoroscopic image sequence can be triggered by electrocardiogram (ECG) at the end diastole (ED) cardiac phase.

At step 112, an IVUS model is initialized in a first frame of the fluoroscopic image sequence. The IVUS model is a semantic model that is built for tracking IVUS devices in the fluoroscopic image sequence. The IVUS devices include a guiding catheter, a guidewire, and an IVUS transducer. The guiding catheter is used to insert the guidewire and IVUS transducer into a vessel. During pullback of the IVUS transducer, the guidewire and IVUS transducer are retracted through the guiding catheter. The guiding catheter tip is typically visible during an intervention, while only a portion of the guiding catheter body may be visible in fluoroscopic images. FIG. 4 illustrates the IVUS model 400 according to an embodiment of the present invention. As illustrated in FIG. 4, the IVUS model 400 includes a guiding catheter body 402, guiding catheter tip 404, guidewire 406, and IVUS transducer 408. The guiding catheter body 402 and the guiding catheter tip 404 are considered separate components in the IVUS model 400 because their appearances are distinguishable in the fluoroscopic images. The guidewire 406 is attached to the IVUS transducer 408 and is used for pulling back the IVUS transducer 408 during interventions. Such a guidewire 406 is typically thin and sometimes is not clearly visible in fluoroscopic images. The guidewire shape is considered the same as the vessel branch shape that is initialized at the angiogram stage. The IVUS transducer 408 is attached on an IVUS catheter, which is a rectangle-like shape in fluoroscopic images.

Returning to FIG. 1, at step 114, the IVUS model is automatically tracked in each remaining frame of the fluoroscopic image sequence. In particular, the IVUS transducer is automatically tracked in each frame of the fluoroscopic image sequence. Since there are continuous breathing motions during the fluoroscopic image acquisition, another point is needed to provide a reference point for registering the IVUS transducer locations. The reference point needs to be stationary relative to the affected breathing motions. According to an advantageous embodiment of the present invention, the guiding catheter tip is used as the reference point, because the guiding catheter tip is a stable and distinguishable point that can be detected in the fluoroscopic images. The tracking of the IVUS model is used to continuously identify the positions of the IVUS transducer and the guiding catheter tip in the frames of the fluoroscopic image sequence. Referring the FIG. 2, images (b) and (c) of FIG. 2 show exemplary results of the initialization and tracking of steps 112 and 114. As shown in image (b) of FIG. 2, a location of an IVUS transducer 204 is detected in a fluoroscopic image. As shown in image (c) of FIG. 2, a location of guiding catheter tip 206 is detected in a fluoroscopic image.

Advantageous embodiments of the present invention utilize a probabilistic framework to address the device tracking problem. According to an advantageous embodiment, this framework includes learning based device detections, a Bayesian tracking scheme, and measurement fusion under a semantic model. The tracking method starts with learning based device detections using four detectors trained from offline annotated training data to detect the IVUS transducer, guiding catheter body, guiding catheter tips, and guidewire body, respectively. Using the detection results as primitive features, the method then performs a model based tracking to locate the IVUS transducer and guidewire tip in each frame of the fluoroscopic image sequence.

Learning based detectors or classifiers are trained from a set of offline training data including both annotated object samples (positive) and non-object samples (negative) to learn the decision boundary that separates the positive and negative training samples. Since the training data includes non-objects as well as objects, trained detectors can distinguish objects from background. According to an embodiment of the present invention, four learning based detectors are trained for device tracking. The four detectors are $P_{IVUS\_trans}$, $P_{cath\_body}$, $P_{cath\_tip}$, and $P_{wire}$, for the IVUS transducer, the guiding catheter body, the guiding catheter tip, and the guidewire body, respectively.

According to an advantageous implementation, a probabilistic boosting tree (PBT) can be used to train each discriminative classifier used in each of the detectors. PBT is a tree based generalization of Adaboost classifiers and can be used to effectively model a complex distribution of a class of objects. The probabilistic outputs of a PBT can be denoted as $P(Z|x)$, where Z is the observed image, and x is the object state (i.e., positive or negative class). The trained classifiers can be trained based on Haar features. Utilizing the idea of Marginal Space Learning (MSL), each of the detectors ($P_{IVUS\_trans}$, $P_{cath\_body}$, $P_{cath\_tip}$, and $P_{wire}$) are constructed using a hierarchical set of discriminative classifiers. For each of the four detectors ($P_{IVUS\_trans}$, $P_{cath\_body}$, $P_{cath\_tip}$, and $P_{wire}$) a position detector is first trained to detect most likely positions of the objects. An orientation detector is then trained at images rotated at different angles to detect the objects at arbitrary orientations. Further, a size detector is trained to search across different scales by varying the size of the Haar features.

Figures 5A, 5B, 5C, 5D:
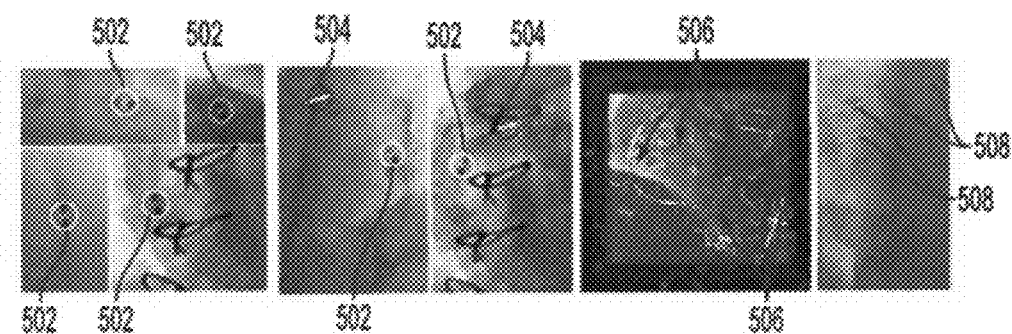
FIG. 5 illustrates exemplary detection results for a IVUS transducer detector, a guiding catheter body detector, a guiding catheter tip detector, and a guidewire body detector.

FIG. 5 illustrates exemplary detection results for the IVUS transducer detector $P_{IVUS\_trans}$, the guiding catheter body detector $P_{cath\_body}$, the guiding catheter tip detector $P_{cath\_tip}$, and the guidewire body detector $P_{wire}$. Image (a) of FIG. 5 shows IVUS transducer detection results 502 in various fluoroscopic images detected using a trained IVUS transducer detector $P_{IVUS\_trans}$. Image (b) of FIG. 5 shows IVUS transducer detection results 502 detected using a trained IVUS transducer detector $P_{IVUS\_trans}$ and guiding catheter tip detection results 504 detected using a trained guiding catheter tip detector $P_{cath\_tip}$ in various fluoroscopic images. In images (a) and (b) multiple detection results for the close to each other are clustered into a single detection result. Image (c) of FIG. 5 shows guidewire segment detection results 506 in a fluoroscopic image detected using a trained guidewire body detector $P_{wire}$. Image (d) of FIG. 5 shows guiding catheter body segment detection results 508 in a fluoroscopic image detected using a trained guiding catheter body detector $P_{cath\_body}$.

It should be noted that the guiding catheter body detector and the guidewire body detector are trained to detect segments of the guiding catheter and guidewire, respectively, not the whole structure. Due to image artifacts and low visibility of devices, false detection of the devices will occur. In order to make the tracking robust to detection errors, a Bayesian tracking framework can be used to integrate multiple detections.

Breathing motions are the dominant motions in the ECG triggered fluoroscopic image sequence, as it can be assumed that there is no cardiac motion between all of the frames acquired at the same cardiac phase. Accordingly, between the ECG triggered frames acquired during the pullback of the IVUS transducer, there exists motion due to breathing. Such breathing motion can be approximated by affine motion. Such motion needs to be compensated in order to register the IVUS transducer to the segmented vessel branch. The breathing motion at the t-th frame is denoted as $M_t=(m_t^x, m_t^y, m_t^r)$, where $m_t^x$, $m_t^y$, $m_t^r$ are the 2D translation and rotation parameters. The motion tracking is expressed as the inference of the motion parameters from the frames of the fluoroscopic image sequence acquired during the pullback of the IVUS transducer. The parameter inference can be formalized in a sequential Bayesian inference framework in order to infer and maximize the posterior probability of the breathing motion parameters given the sequence of fluoroscopic images. Assuming a Markov property for tracking, the posterior probability $P(M_t=(m_t^x, m_t^y, m_t^r)|Z_t)$ can be expressed as:

$$P(M_t|Z_t) \propto P(M_t)P(Z_t|M_t). \quad (1)$$

where $Z_t$ is the observed fluoroscopic image sequence. The tracking result is the motion parameter corresponding to the maximal posterior probability, i.e., $$\hat{M}_t = \underset{M_t}{\mathrm{argmax}} P(M_t|Z_t).$$

In Equation (1), $P(M_t)$ is the prior probability, which can be propagated from previous tracking results. The prior probability can be modeled as:

$$P(M_t) = G(M_t; \Sigma_M), \quad (2)$$

where $G(M_t; \Sigma_M)$ is a Gaussian model with the zero mean and the covariance matrix $\Sigma_M$. The Gaussian model is advantageous because of its simplicity and effectiveness of imposing smoothness constraints for 2D motions. In Equation (1), $P(Z_t|M_t)$ is the likelihood model that measures the likelihood of motion parameters. According to an embodiment of the present invention, the measurement of the likelihood model is a fusion of measurements of the four components of the IVUS model (i.e., the IVUS transducer, the guiding catheter body, the guiding catheter tip, and the guidewire).

Due to the low image quality of fluoroscopy and cluttered backgrounds, independently tracking each device is difficult and prone to detection errors. In order to improve the accuracy and robustness of tracking, embodiments of the present invention combine all of the devices into an integrated IVUS model, in which each component is represented by a curve (e.g., guiding catheter body and guidewire segments) or a point (e.g., guiding catheter tip and IVUS transducer). The integrated IVUS model is denoted as $\Gamma_t$, which can be propagated from the previous frame based on motion parameters, i.e., $\Gamma_t=(\Gamma_{t-1}; M_t)$. The likelihood model can be expressed in the form of curve representations, as $P(Z_t|M_t)=P(Z_t|\Gamma_t)$. Since the integrated IVUS model is combination of multiple components, the measurement model is also a combination multiple measurements of the individual components. However, it is difficult to model the measurement model for a joint set of all components in the model due to the flexibility of individual components and the complexity of their combinations. To simplify the model, it can be assumed that measurements at individual components are independent of each other, i.e., $P(Z_t|\Gamma_t^k,\Gamma_t=P(Z_t|\Gamma_t^k)$, where $\Gamma_t^k$ denotes a component in the integrated model. Accordingly, the measurement model $P(Z_t|\Gamma_t^k)$ can be decomposed into combinations of measurements at individual components, such that:

$$P(Z_t | M_t) = P(Z_t | \Gamma_t) = \sum_k P(Z_t | \Gamma_t^k) P(\Gamma_t^k | \Gamma_t). \quad (3)$$

The component measurements $P(Z_t|\Gamma_t^k)$ are the probability scores resulting from the trained detectors, i.e., $P_{IVUS\_trans}$, $P_{cath\_body}$, $P_{cath\_tip}$, and $P_{wire}$. $P(\Gamma_t^k|\Gamma_t)$ refers to a weight of each individual component in the model, denoting the confidence of individual measurements for that component. Such weights are set empirically.

Figures 6A, 6B, 6C:
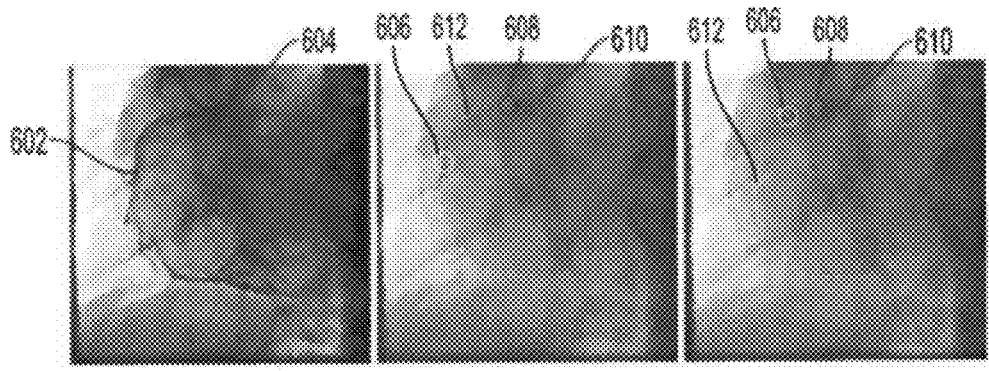
FIG. 6 illustrates initialization and tracking of the integrated IVUS model.

The integrated model to be tracked is initialized from the interactive detection at the angiogram phase. FIG. 6 illustrates initialization and tracking of the integrated IVUS model. As shown in FIG. 6, image (a) shows the vessel branch 602 detected in the contrast-enhances angiogram image. In particular, the interactive detection identifies the centerline of the vessel branch 602, which is used to approximate the shape of the guidewire. As shown in image (a), the guiding catheter body 604 and tip can also be initialized from interactive detections. The IVUS transducer is initialized from detection results in the first frame of the fluoroscopic image sequence. Images (b) and (c) of FIG. 6 show the integrated model initialized and tracked in frames of a fluoroscopic image sequence. As shown in images (b) and (c), the integrated model that is tracked through the frames of the fluoroscopic image sequence includes the IVUS transducer 606, the guiding catheter tip 608, the guiding catheter body 610, and the guidewire 612. During tracking, the model is propagated from a previous frame and updated from the motion parameter estimation. Multiple integrated IVUS model candidates can be generated by shifting and rotating the tracked integrated IVUS model at a previous frame. The candidate points for the IVUS transducer and the guiding catheter tip, can be the candidate segments for the guiding catheter body and the guidewire detected are combined in the current frame by a weighted average of the corresponding probabilities scores of candidate points and segments along an integrated IVUS model candidate. The model motion parameters can be estimated by searching the maximal posterior probability from multiple integrated IVUS model candidates. Exhaustive searching of the motion parameters to maximize posterior probability $P(M_t|Z_t)$ can be computationally expensive. Accordingly, for computational efficiency, a kernel-based multi-resolution method can be applied to implement the tracking.

The model tracking follows the integrated IVUS model's movements caused by breathing motion. A rigid motion model can be used to approximate the breathing motions. The rigid tracking is formulated as maximizing the posterior probability under a rigid motion, i.e., $$\hat{M}_t = \arg_{M_t} \max P(M_t|Z_t). \quad (4)$$

According to an advantageous implementation, a kernel-based multi-resolution tracking method can be used for tracking the integrated IVUS model. In the multi-resolution tracking, measurements can be robustly and efficiently calculated by kernel-based estimation (or smoothing) from a set of samples instead of the whole image. For learning-based measurements, the samples are those points classified positively as belonging to a component of the integrated IVUS model by one of the trained detectors. Markov conditional independency can be assumed such that it can be assumed that the observations at sampling points $x_j^s$ are independent with the un-sampled points $x_i$, i.e., $P(Z_t|x_i,x_j^s)=P(Z_t|x_j^s)$. Thus, the kernel-based measurement estimation can be represented as:

$$P(Z_t | \Gamma_t^k) = \sum_{x_j^s \in \Gamma_t^k} P(Z_t | x_j^s) G_\sigma(x_j^s, x_i), \quad (5)$$

where $P(x_j^s|x_i)=G_\sigma(x_j^s,x_i)$ is a Gaussian kernel with a bandwidth $\sigma$.

Figure 7:
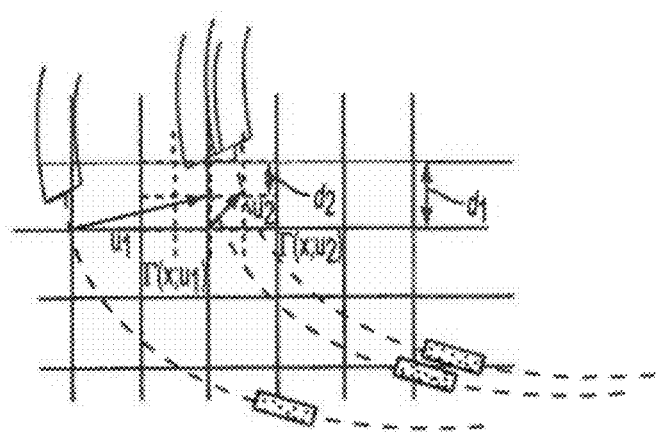
FIG. 7 illustrates multi-resolution tracking with incrementally decreased searching intervals and kernel bandwidths.

The kernel-based measurement estimation can obtain smooth measurements in a neighborhood, reduce computations of measurements, and also allow for multi-resolution searching during rigid and non-rigid tracking by varying bandwidths of the kernels. FIG. 7 illustrates multi-resolution tracking with incrementally decreased searching intervals and kernel bandwidths. As illustrated in FIG. 7, the rigid tracking is performed at multiple resolutions with decreased search intervals $\{d_1>d_2>\ldots>d_T\}$. During the multi-resolution tracking, the corresponding bandwidth in Equation (5) varies accordingly, denoted as $\sigma_t$. At coarse resolutions, larger bandwidths are used to avoid missing tracking caused by larger sampling intervals. At fine resolutions, smaller kernel bandwidths are used to obtain finer tracking results. According to an advantageous implementation, the bandwidth of the kernel can be set as $\sigma_i=d_i$, $i=1,\ldots T$.

Figure 8:
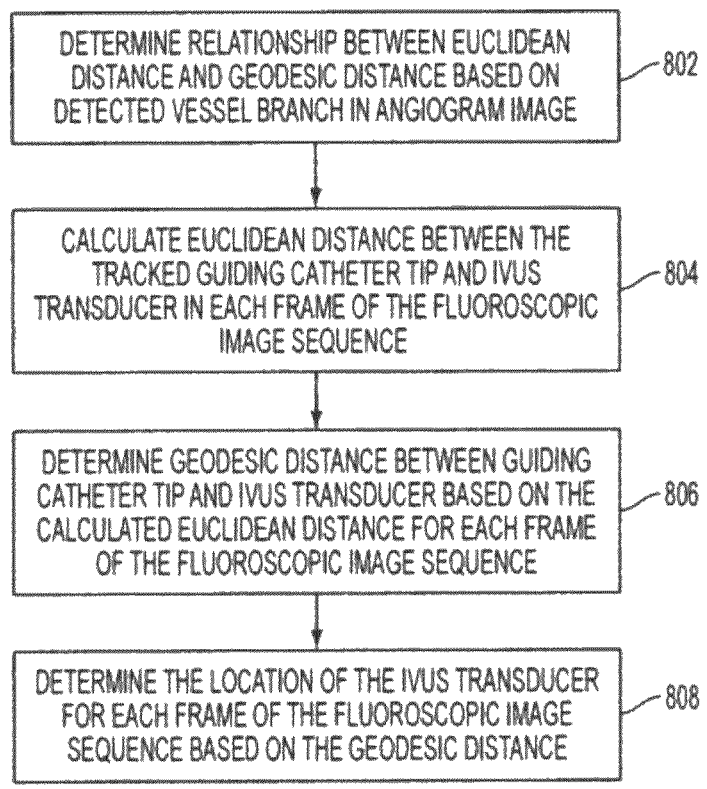
FIG. 8 illustrates a method for mapping the tracker IVUS catheter locations in the fluoroscopic image sequence to the detected vessel branch in the angiogram image according to an embodiment of the present invention.

Returning to FIG. 1, at step 116, the IVUS transducers tracked in each frame of the fluoroscopic image sequence are mapped to the detected vessel branch in the angiogram image. Referring to FIG. 2, image (d) shows a location 208 in the detected vessel branch 202 to which the IVUS transducer 204 is mapped. FIG. 8 illustrates a method for mapping the tracker IVUS catheter locations in the fluoroscopic image sequence to the detected vessel branch in the angiogram image according to an embodiment of the present invention. The method of FIG. 8 can be used to implement step 116 of the method of FIG. 1.

Figure 9A:
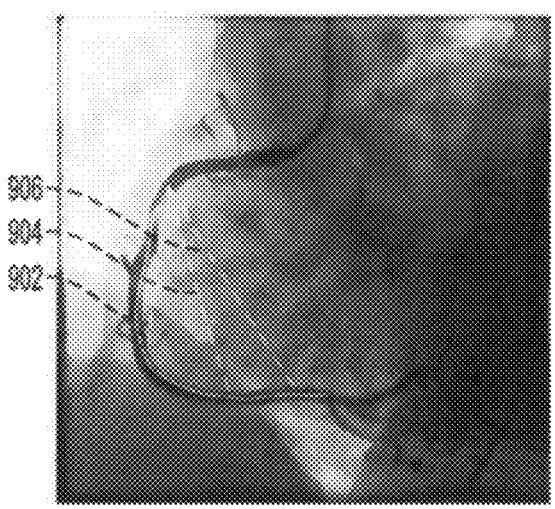
FIG. 9 illustrates a relationship between the Euclidean distance and the geodesic distance for a an exemplary vessel branch.
Figure 9B:
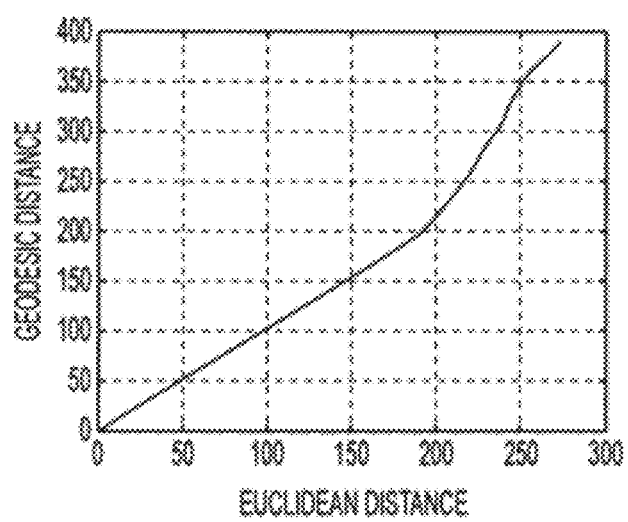

As illustrated in FIG. 8, at step 802, a relationship is determined between Euclidean distance and geodesic distance for the detected vessel branch in the angiogram image. The relationship between the Euclidean distance $D_e(t)$ and the geodesic distance $D_g(t)$ can be expressed as $D_g(t)=f(D_e(t))$, and can be directly calculated from a particular vessel shape, such as the detected vessel branch in the angiogram image. FIG. 9 illustrates an example of determining the relationship between the Euclidean distance and the geodesic distance for a detected vessel branch. In order to calculate this relationship geodesic and Euclidean distances are calculated from the guiding catheter tip to each point on the vessel branch. The Euclidean distance between two points is the length of a straight line connected the two points. As shown in image (a) of FIG. 9, lines 902, 904, and 906 represent the Euclidean distances between the guiding catheter tip and three respective points on the vessel branch. The geodesic distance between the guiding catheter tip and a given point on the vessel branch is the distance from the guiding catheter tip to the point along the shape of the vessel branch. Once the Euclidean and geodesic distances are calculated for each point on the vessel branch, the relationship between the Euclidean and geodesic distances can be established for the vessel branch. Image (b) of FIG. 9 is a graph showing the relationship between the Euclidean distances and the geodesic distances for the vessel branch of image (a) of FIG. 9.

Returning to FIG. 8, at step 804, the Euclidean distance is calculated between the tracked guiding catheter tip and the tracked IVUS transducer in each frame of the fluoroscopic image sequence. At step 806, the geodesic distance between the guiding catheter tip and the IVUS transducer is determined for each frame of the fluoroscopic image sequence based on the corresponding Euclidean distance. In particular, the geodesic distance $D_g(t)$ between a tracked guiding catheter tip and a tracked IVUS transducer can be inferred from the Euclidean distance $D_e(t)$ between the guiding catheter tip and the IVUS transducer using the relationship $D_g(t)=f(D_e(t))$ determined at step 802. However, the function $f(D_e(t))$ may not be a single-valued function for some vessel shapes, which means for a particular calculated Euclidean distance, there could be multiple corresponding geodesic distances. In order to resolve any ambiguity in estimating the geodesic distance from the Euclidean distance, a smoothness constraint can be imposed in order to require that the geodesic distance be smoothly changed between successive frames. This smoothness constraint can be used to select the best geodesic distance from all possible candidates in each frame.

At step 808, the location of the IVUS transducer in the detected vessel branch of the angiogram image is determined for each frame of the fluoroscopic image sequence. As described above, the geodesic distance between the guiding catheter tip and the IVUS transducer is the distance from the guiding catheter tip along the detected vessel branch. Accordingly, the location in the detected vessel branch of the tracked IVUS transducer for each frame of the fluoroscopic image sequence can be determined by determining the location in the angiogram image that is the corresponding geodesic distance from the guiding catheter tip along the detected vessel branch in the angiogram image. According to an advantageous implementation, a pulling-back model may be fitted to the determined locations of the IVUS transducer in order to estimate the motion of the IVUS transducer in the vessel branch. The model fitting serves various purposes. For example, the motion directly observed from the geodesic distances can be noisy. Such noise may be due to vessel foreshortening, breathing motions, imperfect ECG gating, and/or possible catheter movements inside the vessel. A smooth model fitted on the estimated geodesic distances can help reduce the impact of such factors on the registration. Further, the model fitting can identify false detections and tracking errors as outliers of the fitted model. Such errors can then be removed from motion estimations. The outlier identification and model fitting can is then iterated, thereby improving the registration accuracy. The tracked IVUS transducer from each frame of the fluoroscopic image sequence is then mapped to a point on the segmented vessel branch by matching the fitted pulling-back geodesic distance.

Figure 10A:
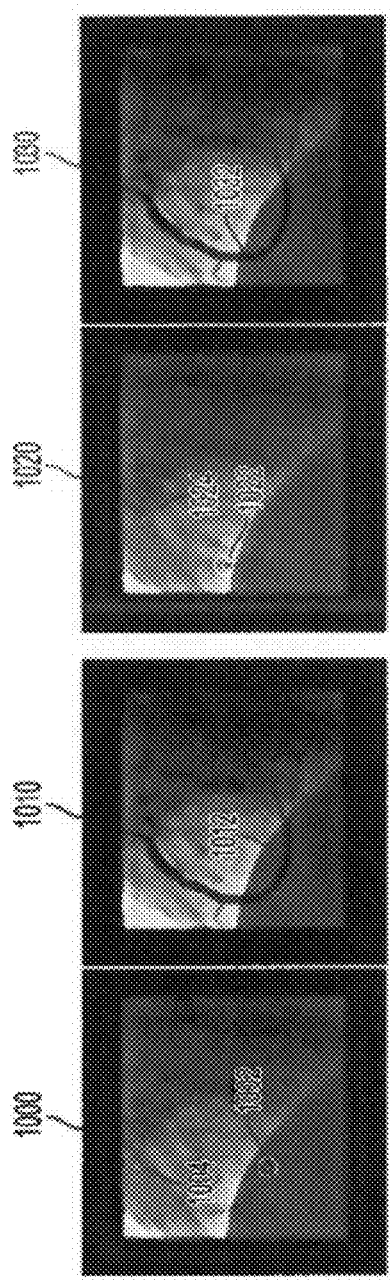
FIG. 10 illustrated exemplary results of mapping tracked IVUS transducers to a detected vessel branch in an angiogram image.
Figure 10B:
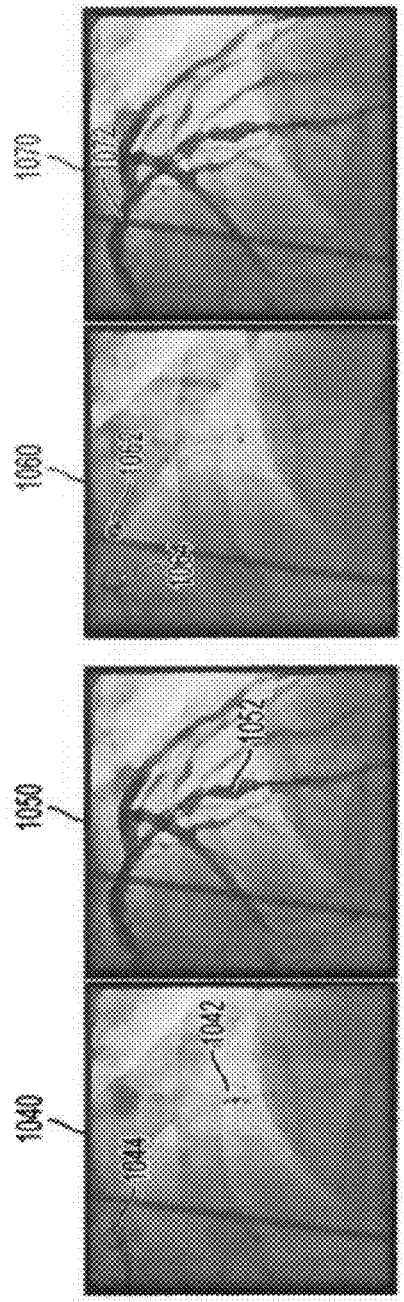

FIG. 10 illustrated exemplary results of mapping tracked IVUS transducers to a detected vessel branch in an angiogram image. As illustrated in FIG. 10, image sets (a) and (b) shows tracking results mapped to a detected vessel branch of an angiogram. As shown in image set (a), image 1000 is a first fluoroscopic image frame in which an IVUS transducer 1002 and a guiding catheter tip 1004 have been tracked, and image 1010 is an angiogram image that shows the corresponding location 1012 of IVUS transducer 1002 in a detected vessel branch. Image 1020 is a second fluoroscopic image frame in which an IVUS transducer 1022 and a guiding catheter tip 1024 have been tracked, and image 1030 is an angiogram image that shows the corresponding location 1032 of IVUS transducer 1022 in a detected vessel branch. As shown in image set (b), image 1040 is a first fluoroscopic image frame in which an IVUS transducer 1042 and a guiding catheter tip 1044 have been tracked, and image 1050 is an angiogram image that shows the corresponding location 1052 of IVUS transducer 1042 in a detected vessel branch. Image 1060 is a second fluoroscopic image frame in which an IVUS transducer 1062 and a guiding catheter tip 1064 have been tracked, and image 1070 is an angiogram image that shows the corresponding location 1072 of IVUS transducer 1062 in a detected vessel branch.

Returning to FIG. 1, at step 118, the IVUS images acquired during the pullback of the IVUS transducer are registered to the detected vessel branch in the angiogram image. Each IVUS image can be associated with a frame of the fluoroscopic image sequence by matching timestamps of the IVUS images and fluoroscopic image sequence frames. Each IVUS image can then be directly registered with the point in the detected vessel branch of the angiogram image that corresponds to IVUS transducer of the associated fluoroscopic image frame.

At step 120, the angiography and IVUS co-registration results are output. The results can be output by displaying the results, for example, on a display device of computer system used to implement the method. It is also possible to output the results by storing the co-registration results, for example, in a memory or storage of a computer system of on a computer readable medium.

Figure 11A:
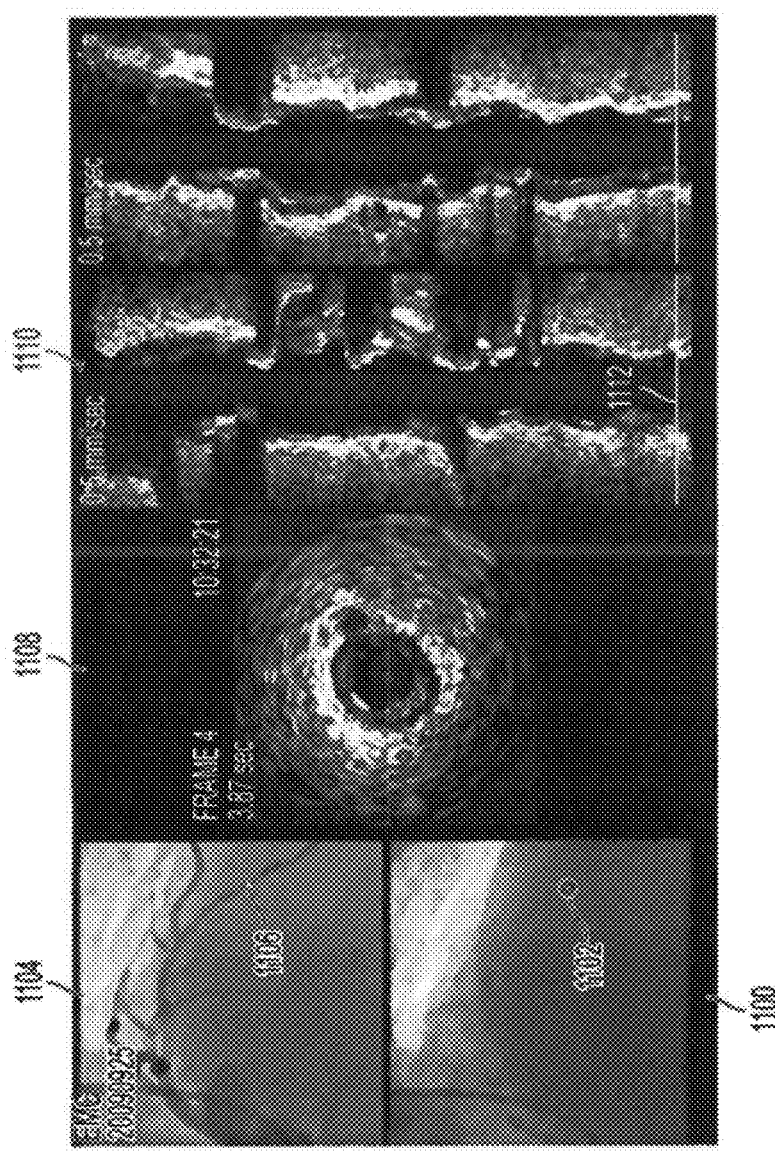
FIGS. 11A-11C illustrated exemplary angiography and IVUS co-registration results.
Figure 11B:
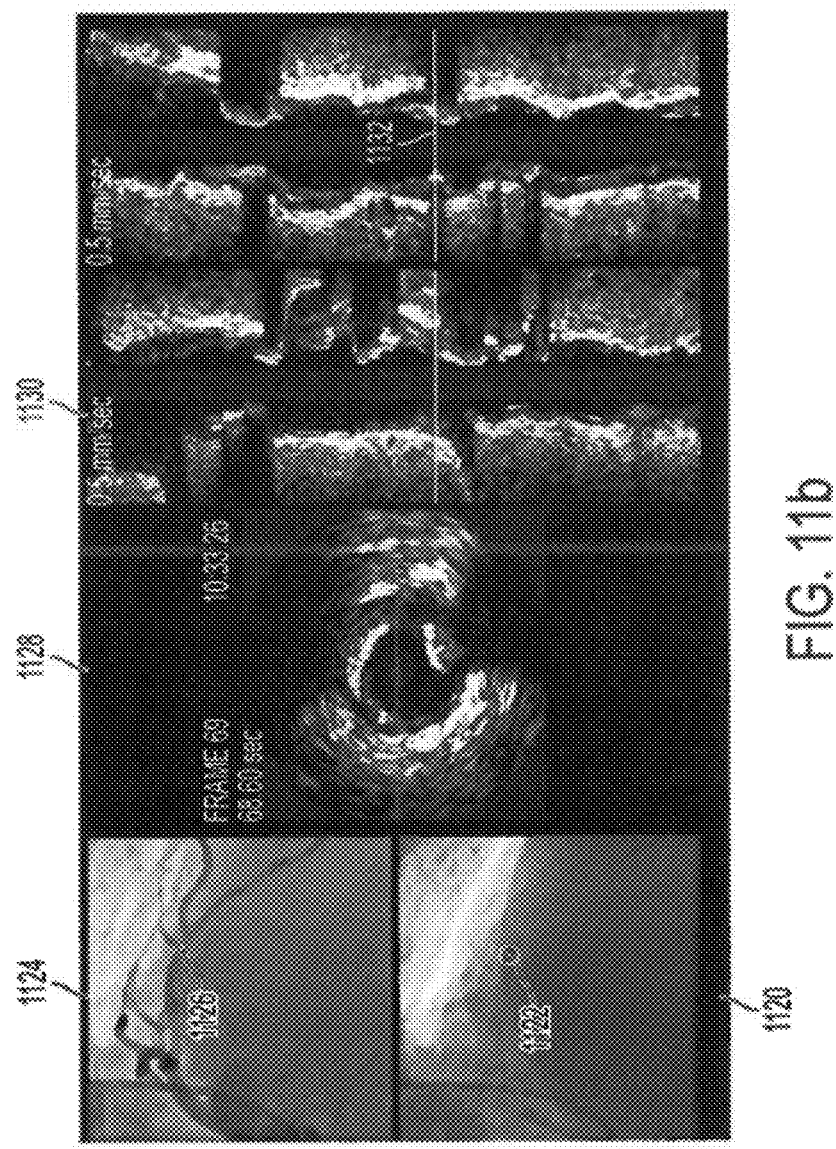
Figure 11C:
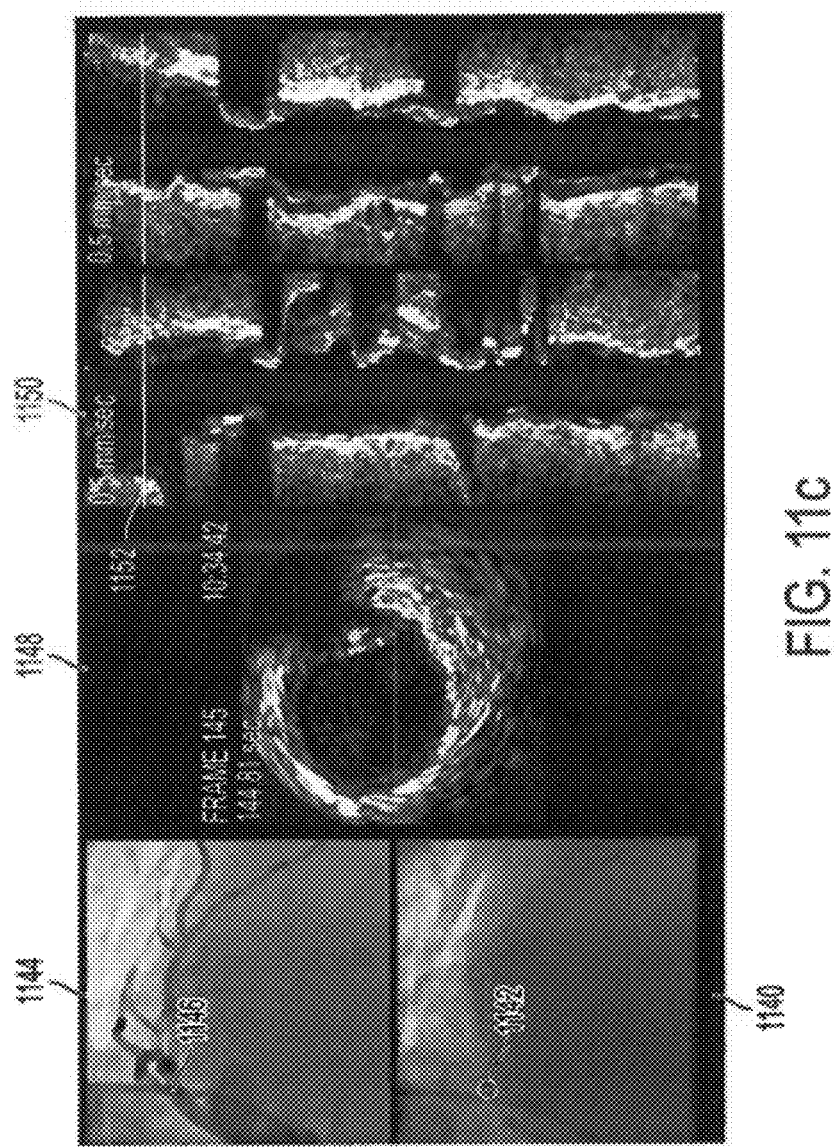

FIGS. 11A-11C illustrated exemplary angiography and IVUS co-registration results. The results illustrated in FIGS. 11A-11C show the registration at three different points during the pullback of an IVUS transducer. As shown in FIG. 11A, image 1100 is a fluoroscopic image showing the tracked IVUS transducer 1102. Image 1104 is an angiogram image showing the registered location 1106 of IVUS transducer 1102 in a vessel branch. Image 1108 is a cross-sectional view of an IVUS image that is registered to location 1102 in the vessel branch. Image 1110 is an axial view of the IVUS image and line 1112 in the axial view 1110 corresponds to location 1106 in the vessel branch. As shown in FIG. 11B, image 1120 is a fluoroscopic image showing the tracked IVUS transducer 1122. Image 1124 is an angiogram image showing the registered location 1126 of IVUS transducer 1122 in a vessel branch. Image 1128 is a cross-sectional view of an IVUS image that is registered to location 1122 in the vessel branch. Image 1130 is an axial view of the IVUS image and line 1132 in the axial view 1130 corresponds to location 1126 in the vessel branch. As shown in FIG. 11C, image 1140 is a fluoroscopic image showing the tracked IVUS transducer 1142. Image 1144 is an angiogram image showing the registered location 1146 of IVUS transducer 1142 in a vessel branch. Image 1148 is a cross-sectional view of an IVUS image that is registered to location 1142 in the vessel branch. Image 1150 is an axial view of the IVUS image and line 1152 in the axial view 1150 corresponds to location 1146 in the vessel branch.

Figure 12:
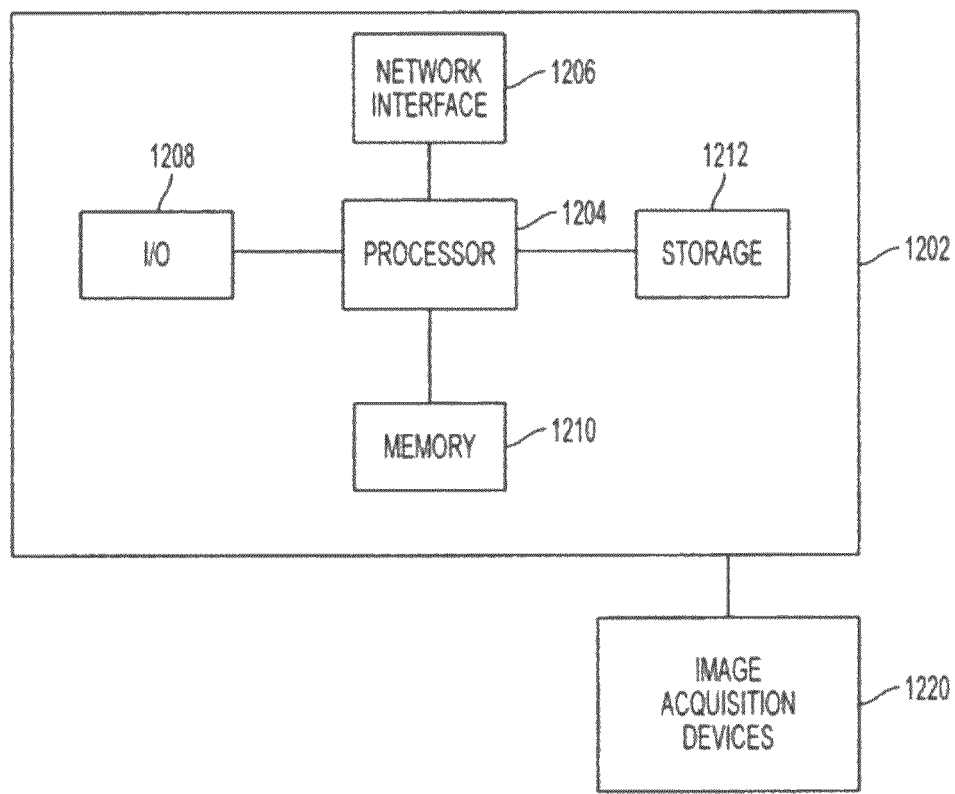
FIG. 12 is a high level block diagram of a computer capable of implementing the present invention.

The above-described methods for angiography and IVUS co-registration may be implemented on a computer using well-known computer processors, memory units, storage devices, computer software, and other components. A high level block diagram of such a computer is illustrated in FIG. 12. Computer 1202 contains a processor 1204 which controls the overall operation of the computer 1202 by executing computer program instructions which define such operation.

The computer program instructions may be stored in a storage device 1212, or other computer readable medium, (e.g., magnetic disk) and loaded into memory 1210 when execution of the computer program instructions is desired. Thus, all method steps described above, including the method steps illustrated in FIGS. 1, 3, and 8, may be defined by the computer program instructions stored in the memory 1210 and/or storage 1212 and controlled by the processor 1204 executing the computer program instructions. Image acquisition devices 1220, such as an X-ray imaging device and an IVUS transducer, can be connected to the computer 1202 to input fluoroscopic image sequences to the computer 1202. It is possible to implement some image acquisition devices 1220 with the computer 1202 as one device. It is also possible that the image acquisition devices 1220 and the computer 1202 communicate wirelessly through a network or using any other type of communication protocol. The computer 1202 also includes one or more network interfaces 1206 for communicating with other devices via a network. The computer 1202 also includes other input/output devices 1208 that enable user interaction with the computer 1202 (e.g., display, keyboard, mouse, speakers, buttons, etc.) One skilled in the art will recognize that an implementation of an actual computer could contain other components as well, and that FIG. 12 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method for angiography and intra-vascular ultrasound (IVUS) co-registration comprising:
   detecting a vessel branch in an angiogram image;
   receiving a sequence of IVUS images from an IVUS transducer, the IVUS image acquired while the IVUS transducer is being pulled back through the vessel branch;
   receiving a fluoroscopic image sequence acquired while the IVUS transducer is being pulled back through the vessel branch;
   detecting the IVUS transducer and a guiding catheter tip in each of a plurality of frames of the fluoroscopic image sequence;
   mapping the IVUS transducer detected in each frame of the fluoroscopic image sequence to a respective location in the detected vessel branch of the angiogram image based on a calculated Euclidean distance and a determined geodesic distance between the IVUS transducer detected in each frame and the guiding catheter tip detected in each frame; and
   registering each of the IVUS images to a respective location in the detected vessel branch of the angiogram image based on the mapped location of the IVUS transducer detected in a corresponding frame of the fluoroscopic image sequence.

2. The method of claim 1, wherein the step of detecting the IVUS transducer and a guiding catheter tip in each of a plurality of frames of the fluoroscopic image sequence comprises:
   initializing an integrated IVUS model in a first frame of the fluoroscopic image sequence; and
   tracking the integrated IVUS model in each remaining frame of the fluoroscopic image sequence.

3. The method of claim 2, wherein the integrated IVUS model comprises the IVUS transducer, the guiding catheter tip, a guiding catheter body, and a guidewire.

4. The method of claim 3, wherein the step of tracking the integrated IVUS model in each remaining frame of the fluoroscopic image sequence comprises:
   detecting candidate points for the IVUS transducer and the guiding catheter tip and candidate segments for the guiding catheter body and the guidewire in each remaining frame using trained IVUS transducer, guiding catheter tip, guiding catheter body, a guidewire detectors, respectively; and
   tracking the integrated IVUS model using a computer vision based method.

5. The method of claim 4, wherein the step of tracking the integrated IVUS model using a computer vision based method comprises:
   generating multiple integrated IVUS model candidates by shifting and rotating the tracked integrated IVUS model at a previous frame;
   combining the candidate points for the IVUS transducer and the guiding catheter tip, and the candidate segments for the guiding catheter body and the guidewire detected in the current frame by a weighted average of the corresponding probabilities scores of candidate points and segments along an integrated IVUS model candidate; and
   estimating the model motion parameters by searching the maximal posterior probability from multiple integrated IVUS model candidates.

6. The method of claim 2, wherein the step of tracking the integrated IVUS model in each remaining frame of the fluoroscopic image sequence comprises:
   tracking the integrated IVUS model using kernel-based multi-resolution tracking.

7. The method of claim 1, wherein the step of mapping the IVUS transducer detected in each frame of the fluoroscopic image sequence to a respective location in the detected vessel branch of the angiogram image based on a calculated Euclidean distance and a determined geodesic distance between the IVUS transducer detected in each frame and the guiding catheter tip detected in each frame comprises:
   determining a relationship between Euclidean distance and geodesic distance from a location of the guiding catheter tip to each of a plurality of points on the detected vessel branch of the angiogram image;
   calculating the Euclidean distance between the IVUS transducer and the guiding catheter tip detected in each frame of the fluoroscopic image sequence;
   determining the geodesic distance corresponding to the IVUS transducer detected in each frame of the fluoroscopic image sequence based on the determined relationship between Euclidean distance and geodesic distance for the detected vessel branch; and
   determining the respective location in the detected vessel branch for the IVUS transducer detected in each frame of the fluoroscopic image sequence based on the corresponding geodesic distance.

8. The method of claim 7, wherein the step of determining a relationship between Euclidean distance and geodesic distance from a location of the guiding catheter tip to each of a plurality of points on the detected vessel branch of the angiogram image comprises:
   calculating the Euclidean distances and the geodesic distances between a location of the guiding catheter tip and each of the plurality of points on the detected vessel branch in the angiogram image.

9. The method of claim 7, wherein the step of determining a geodesic distance corresponding to the IVUS transducer detected in each frame of the fluoroscopic image sequence based on the determined relationship between Euclidean distance and geodesic distance for the detected vessel branch comprises:
   determining at least one geodesic distance candidate for the IVUS transducer detected in each frame of the fluoroscopic image sequence;
   selecting one geodesic distance candidate for the IVUS transducer detected in each frame of the fluoroscopic image sequence based on a smoothness constraint between the geodesic distances determined for successive frames.

10. The method of claim 7, wherein the step of determining the respective location in the detected vessel branch for the IVUS transducer detected in each frame of the fluoroscopic image sequence based on the corresponding geodesic distance comprises:
    fitting a smooth pulling-back model on the geodesic distances determined for the IVUS transducer in the frames of the fluoroscopic image sequence; and
    mapping the IVUS transducer detected in each frame of the fluoroscopic image sequence to the respective location in the vessel branch based on the fitted pulling-back model.

11. The method of claim 1, wherein the step of registering each of the IVUS images to a respective location in the detected vessel branch of the angiogram image based on the mapped location of the IVUS transducer detected in a corresponding frame of the fluoroscopic image sequence comprises:
    synchronizing each of the IVUS images with a corresponding frame of the fluoroscopic image sequence based on timestamps of the IVUS images and the fluoroscopic image sequence; and
    registering each IVUS image to the respective location to which the IVUS transducer detected in the corresponding frame of the fluoroscopic image sequence is mapped.

12. An apparatus for angiography and intra-vascular ultrasound (IVUS) co-registration comprising:
    means for detecting a vessel branch in an angiogram image;
    means for receiving a sequence of IVUS images from an IVUS transducer, the IVUS image acquired while the IVUS transducer is being pulled back through the vessel branch;
    means for receiving a fluoroscopic image sequence acquired while the IVUS transducer is being pulled back through the vessel branch;
    means for detecting the IVUS transducer and a guiding catheter tip in each of a plurality of frames of the fluoroscopic image sequence;
    means for mapping the IVUS transducer detected in each frame of the fluoroscopic image sequence to a respective location in the detected vessel branch of the angiogram image based on a calculated Euclidean distance and a determined geodesic distance between the IVUS transducer detected in each frame and the guiding catheter tip detected in each frame and
    means for registering each of the IVUS images to a respective location in the detected vessel branch of the angiogram image based on the mapped location of the IVUS transducer detected in a corresponding frame of the fluoroscopic image sequence.

13. The apparatus of claim 12, wherein the means for detecting the IVUS transducer and a guiding catheter tip in each of a plurality of frames of the fluoroscopic image sequence comprises:
    means for initializing an integrated IVUS model in a first frame of the fluoroscopic image sequence; and
    means for tracking the integrated IVUS model in each remaining frame of the fluoroscopic image sequence.

14. The apparatus of claim 13, wherein the integrated IVUS model comprises the IVUS transducer, the guiding catheter tip, a guiding catheter body, and a guidewire.

15. The apparatus of claim 14, wherein the means for tracking the integrated IVUS model in each remaining frame of the fluoroscopic image sequence comprises:
    means for detecting candidate points for the IVUS transducer and the guiding catheter tip and candidate segments for the guiding catheter body and the guidewire in each remaining frame using trained IVUS transducer, guiding catheter tip, guiding catheter body, a guidewire detectors, respectively; and
    means for tracking the integrated IVUS model using a computer vision based method.

16. The apparatus of claim 15, wherein the means for tracking the integrated IVUS model using a computer vision based method comprises:
    means for generating multiple integrated IVUS model candidates by shifting and rotating the tracked integrated IVUS model at a previous frame;
    means for combining the candidate points for the IVUS transducer and the guiding catheter tip, and the candidate segments for the guiding catheter body and the guidewire detected in the current frame by a weighted average of the corresponding probabilities scores of candidate points and segments along an integrated IVUS model candidate; and
    means for estimating the model motion parameters by searching the maximal posterior probability from multiple integrated IVUS model candidates.

17. The apparatus of claim 13, wherein the means for tracking the integrated IVUS model in each remaining frame of the fluoroscopic image sequence comprises:
    means for tracking the integrated IVUS model using kernel-based multi-resolution tracking.

18. The apparatus of claim 12, wherein the means for mapping the IVUS transducer detected in each frame of the fluoroscopic image sequence to a respective location in the detected vessel branch of the angiogram image based on a calculated Euclidean distance and a determined geodesic distance between the IVUS transducer detected in each frame and the guiding catheter tip detected in each frame comprises:
    means for determining a relationship between Euclidean distance and geodesic distance from a location of the guiding catheter tip to each of a plurality of points on the detected vessel branch of the angiogram image;
    means for calculating the Euclidean distance between the IVUS transducer and the guiding catheter tip detected in each frame of the fluoroscopic image sequence;
    means for determining the geodesic distance corresponding to the IVUS transducer detected in each frame of the fluoroscopic image sequence based on the determined relationship between Euclidean distance and geodesic distance for the detected vessel branch; and means for determining the respective location in the detected vessel branch for the IVUS transducer detected in each frame of the fluoroscopic image sequence based on the corresponding geodesic distance.

19. The apparatus of claim 18, wherein the means for determining a relationship between Euclidean distance and geodesic distance from a location of the guiding catheter tip to each of a plurality of points on the detected vessel branch of the angiogram image comprises:

means for calculating the Euclidean distances and the geodesic distances between a location of the guiding catheter tip and each of the plurality of points on the detected vessel branch in the angiogram image.

20. The apparatus of claim 18, wherein the means for determining a geodesic distance corresponding to the IVUS transducer detected in each frame of the fluoroscopic image sequence based on the determined relationship between Euclidean distance and geodesic distance for the detected vessel branch comprises:

means for determining at least one geodesic distance candidate for the IVUS transducer detected in each frame of the fluoroscopic image sequence;

means for selecting one geodesic distance candidate for the IVUS transducer detected in each frame of the fluoroscopic image sequence based on a smoothness constraint between the geodesic distances determined for successive frames.

21. The apparatus of claim 18, wherein the means for determining the respective location in the detected vessel branch for the IVUS transducer detected in each frame of the fluoroscopic image sequence based on the corresponding geodesic distance comprises:

means for fitting a smooth pulling-back model on the geodesic distances determined for the IVUS transducer in the frames of the fluoroscopic image sequence; and means for mapping the IVUS transducer detected in each frame of the fluoroscopic image sequence to the respective location in the vessel branch based on the fitted pulling-back model.

22. The apparatus of claim 12, wherein the means for registering each of the IVUS images to a respective location in the detected vessel branch of the angiogram image based on the mapped location of the IVUS transducer detected in a corresponding frame of the fluoroscopic image sequence comprises:

means for synchronizing each of the IVUS images with a corresponding frame of the fluoroscopic image sequence based on timestamps of the IVUS images and the fluoroscopic image sequence; and means for registering each IVUS image to the respective location to which the IVUS transducer detected in the corresponding frame of the fluoroscopic image sequence is mapped.

23. A non-transitory computer readable medium encoded with computer executable instructions for angiography and intra-vascular ultrasound (IVUS) co-registration, the computer executable instructions defining steps comprising:

detecting a vessel branch in an angiogram image;

receiving a sequence of IVUS images from an IVUS transducer, the IVUS image acquired while the IVUS transducer is being pulled back through the vessel branch;

receiving a fluoroscopic image sequence acquired while the IVUS transducer is being pulled back through the vessel branch;

detecting the IVUS transducer and a guiding catheter tip in each of a plurality of frames of the fluoroscopic image sequence;

mapping the IVUS transducer detected in each frame of the fluoroscopic image sequence to a respective location in the detected vessel branch of the angiogram image based on a calculated Euclidean distance and a determined geodesic distance between the IVUS transducer detected in each frame and the guiding catheter tip detected in each frame; and registering each of the IVUS images to a respective location in the detected vessel branch of the angiogram image based on the mapped location of the IVUS transducer detected in a corresponding frame of the fluoroscopic image sequence.

24. The computer readable medium of claim 23, wherein the computer executable instructions defining the step of detecting the IVUS transducer and a guiding catheter tip in each of a plurality of frames of the fluoroscopic image sequence comprise computer executable instructions defining the steps of:

initializing an integrated IVUS model in a first frame of the fluoroscopic image sequence; and tracking the integrated IVUS model in each remaining frame of the fluoroscopic image sequence.

25. The computer readable medium of claim 24, wherein the integrated IVUS model comprises the IVUS transducer, the guiding catheter tip, a guiding catheter body, and a guidewire.

26. The computer readable medium of claim 25, wherein the computer executable instructions defining the step of tracking the integrated IVUS model in each remaining frame of the fluoroscopic image sequence comprise computer executable instructions defining the steps of:

detecting candidate points for the IVUS transducer and the guiding catheter tip and candidate segments for the guiding catheter body and the guidewire in each remaining frame using trained IVUS transducer, guiding catheter tip, guiding catheter body, a guidewire detectors, respectively; and tracking the integrated IVUS model using a computer vision based method.

27. The computer readable medium of claim 26, wherein the computer executable instructions defining the step of tracking the integrated IVUS model using a computer vision based method comprise computer executable instructions defining the steps of:

generating multiple integrated IVUS model candidates by shifting and rotating the tracked integrated IVUS model at a previous frame;

combining the candidate points for the IVUS transducer and the guiding catheter tip, and the candidate segments for the guiding catheter body and the guidewire detected in the current frame by a weighted average of the corresponding probabilities scores of candidate points and segments along an integrated IVUS model candidate; and estimating the model motion parameters by searching the maximal posterior probability from multiple integrated IVUS model candidates.

28. The computer readable medium of claim 24, wherein the computer executable instructions defining the step of tracking the integrated IVUS model in each remaining frame of the fluoroscopic image sequence comprise computer executable instructions defining the step of:

tracking the integrated IVUS model using kernel-based multi-resolution tracking.

29. The computer readable medium of claim 23, wherein the computer executable instructions defining the step of mapping the IVUS transducer detected in each frame of the fluoroscopic image sequence to a respective location in the detected vessel branch of the angiogram image based on a calculated Euclidean distance and a determined geodesic distance between the IVUS transducer detected in each frame and the guiding catheter tip detected in each frame comprise computer executable instructions defining the steps of:
- determining a relationship between Euclidean distance and geodesic distance from a location of the guiding catheter tip to each of a plurality of points on the detected vessel branch of the angiogram image;
- calculating the Euclidean distance between the IVUS transducer and the guiding catheter tip detected in each frame of the fluoroscopic image sequence;
- determining the geodesic distance corresponding to the IVUS transducer detected in each frame of the fluoroscopic image sequence based on the determined relationship between Euclidean distance and geodesic distance for the detected vessel branch; and
- determining the respective location in the detected vessel branch for the IVUS transducer detected in each frame of the fluoroscopic image sequence based on the corresponding geodesic distance.

30. The computer readable medium of claim 29, wherein the computer executable instructions defining the step of determining a relationship between Euclidean distance and geodesic distance from a location of the guiding catheter tip to each of a plurality of points on the detected vessel branch of the angiogram image comprise computer executable instructions defining the step of:
- calculating the Euclidean distances and the geodesic distances between a location of the guiding catheter tip and each of the plurality of points on the detected vessel branch in the angiogram image.

31. The computer readable medium of claim 29, wherein the computer executable instructions defining the step of determining a geodesic distance corresponding to the IVUS transducer detected in each frame of the fluoroscopic image sequence based on the determined relationship between Euclidean distance and geodesic distance for the detected vessel branch comprise computer executable instructions defining the steps of:
- determining at least one geodesic distance candidate for the IVUS transducer detected in each frame of the fluoroscopic image sequence;
- selecting one geodesic distance candidate for the IVUS transducer detected in each frame of the fluoroscopic image sequence based on a smoothness constraint between the geodesic distances determined for successive frames.

32. The computer readable medium of claim 29, wherein the computer executable instructions defining the step of determining the respective location in the detected vessel branch for the IVUS transducer detected in each frame of the fluoroscopic image sequence based on the corresponding geodesic distance comprise computer executable instructions defining the steps of:
- fitting a smooth pulling-back model on the geodesic distances determined for the IVUS transducer in the frames of the fluoroscopic image sequence; and
- mapping the IVUS transducer detected in each frame of the fluoroscopic image sequence to the respective location in the vessel branch based on the fitted pulling-back model.

33. The computer readable medium of claim 23, wherein the computer executable instructions defining the step of registering each of the IVUS images to a respective location in the detected vessel branch of the angiogram image based on the mapped location of the IVUS transducer detected in a corresponding frame of the fluoroscopic image sequence comprise computer executable instructions defining the steps of:
- synchronizing each of the IVUS images with a corresponding frame of the fluoroscopic image sequence based on timestamps of the IVUS images and the fluoroscopic image sequence; and
- registering each IVUS image to the respective location to which the IVUS transducer detected in the corresponding frame of the fluoroscopic image sequence is mapped.

* * * * *